(12) United States Patent
Lawandy

(10) Patent No.: US 7,355,704 B2
(45) Date of Patent: Apr. 8, 2008

(54) CHEMICAL AND BIOLOGICAL SENSING USING METALLIC PARTICLES IN AMPLIFYING AND ABSORBING MEDIA

(75) Inventor: Nabil M. Lawandy, Saunderstown, RI (US)

(73) Assignee: Solaris Nanosciences, Inc., Providence, RI (US)

( * ) Notice: Subject to any disclaimer, the term of this patent is extended or adjusted under 35 U.S.C. 154(b) by 0 days.

(21) Appl. No.: 11/452,454

(22) Filed: Jun. 13, 2006

(65) Prior Publication Data

US 2007/0177140 A1    Aug. 2, 2007

Related U.S. Application Data

(60) Provisional application No. 60/689,850, filed on Jun. 13, 2005.

(51) Int. Cl.
*G01J 3/44* (2006.01)
*G01N 21/65* (2006.01)

(52) U.S. Cl. ..................................................... 356/301

(58) Field of Classification Search .................. 356/301
See application file for complete search history.

(56) References Cited

U.S. PATENT DOCUMENTS 5,864,397 A * 1/1999 Vo-Dinh ...................... 356/301
2003/0059820 A1 * 3/2003 Vo-Dinh ........................ 435/6

* cited by examiner

*Primary Examiner*—F. L. Evans
*Assistant Examiner*—Abdullahi Nur
(74) *Attorney, Agent, or Firm*—Kirkpatrick & Lockhart Preston Gates Ellis LLP

(57) ABSTRACT

A film for surface enhanced raman scattering may be utilized for chemical and biological sensing. The film includes a polymeric layer, and a metallic nanoparticle having a cross-section, the metallic nanoparticle being embedded in the polymeric layer. The polymeric layer has a thickness less than a largest straight line through the cross-section of said metallic nanoparticle. The polymeric layer is selected from a group of absorbing media and amplifying media, and the metallic nanoparticle may be gold. The metallic nanoparticle may also be a shape selected from a group of spheroids and rods.

4 Claims, 6 Drawing Sheets

CHEMICAL AND BIOLOGICAL SENSING USING METALLIC PARTICLES IN AMPLIFYING AND ABSORBING MEDIA

This application claims priority to Provisional application U.S. Ser. No. 60/689,850 filed Jun. 13, 2005, the entirety of which is herein incorporated by reference.

BACKGROUND

Since the discovery of Surface Enhanced Raman Scattering (SERS) on rough silver electrodes, a large volume of work has gone into enhancing this effect with the aim of developing ultra sensitive detection of chemical and biological molecules. Of particular interest are chemical agents used in warfare and biological molecules related to genomic applications and disease agents.

Several approaches to designing SERS substrates based around metallic nanopoparticles and patterned surfaces have been developed. In all of these approaches, the basic guiding physics has been the use of plasmon resonance to enhance local fields along with charge transfer effects which enhance the matrix elements of the Raman process.

Recent work by Lawandy has shown that large field enhancements beyond the conventional effect in non-resonant media such as liquids and transparent solids can take place when the metallic particles (small compared to the wavelengths of interest) are placed in or near amplifying media. In this work, the case of a plasmon resonance resonant with the gain medium response was treated in the Drude Model limit of the metallic particle electronic response. It can also be shown that the use of anisotropic metallic particles such as spheroids and rods of varying aspect ratios can be used to tune the required gain or amplification required to create the large external fields.

Subsequent work has shown that the amplifying medium effect is present in cases of finite particle size and beyond the electrostatic limit of the particle modes. This basic effect of gain and localized plasmon excitations can be further combined with the electromagnetic properties of arrays and photonic band gap structures to provide additional effects on the density of photon states and provide additional enhancements as well as filtering effects useful for the development of chem-bio sensors utilizing amplifying media to create gigantic molecular detection sensitivities.

Further developments have shown that the nanoparticle plasmon resonances on a passive substrate need not be resonant or overlap the gain or absorption medium's resonance. FIGS. 1a and 1b show how the local square of the electric field just outside the particle surface is enhanced in the case of a particle surrounded by a dye film absorbing near and at a frequency far away form the plasmon resonance for the particles on the substrate alone (glass for example) respectfully.

When the film is thick enough (~0.5 nm), the plasmon response and the external field are driven by the dielectric functions of the dye film and not the substrate. This important fact means that the response takes place at or near the absorbing or amplifying medium's resonances and not the bare plasmon resonance. This in turn means that a number of different metallic particles can be used with virtually any gain or absorption (or both) medium to tune the enhancement to where it is needed for the specific application such as SERS. A large part of this enhancement is due to a factor relating the external field to the internal particle field which is inversely proportional to the highly dispersive absorbing/amplifying medium dielectric functions when the strength of this response is sufficiently strong. Typically this occurs in solid films of high density FIG. 2 shows a silicon substrate with a random collection of gold nanoparticles prior to the deposition of an absorbing or amplifying film.

The use of a thin (~0.5 nm-10 nm) film of absorber around a metallic particle results in dramatic enhancements in the field just outside the thin absorber layer. This enhancement is considerably larger than that of the case of a nanoparticle surrounded by a shell of transparent material with no sharp dispersions lines associated with the absorbing transition. FIG. 3 shows the dielectric functions for a solid film of dye coating the particles in FIG. 1. It is clear from these two figures that the enhancement occurs near the absorption resonances and in particular near the dips in the real part of the absorber susceptibility.

SUMMARY OF THE INVENTION

Provided herein is a film for surface enhanced raman scattering. The film includes a polymeric layer, and a metallic nanoparticle having a cross-section, the metallic nanoparticle being embedded in the polymeric layer. The polymeric layer has a thickness less than a largest straight line through the cross-section of said metallic nanoparticle. The polymeric layer is selected from a group of absorbing media and amplifying media, and the metallic nanoparticle may be gold. The metallic nanoparticle may also be a shape selected from a group of spheroids and rods.

DETAILED DESCRIPTION OF THE INVENTION

An important feature of any SERS substrate is its ability to provide analyte binding to specific chemical or biological moieties. In order to realize this while also creating an enhanced surface field due to the presence of the amplifying or resonant absorbing medium surrounding the metallic particle or surface feature, we disclose the use of a substrate comprised of a substrate which is transparent or absorbing, a collection of metallic nanoparticles, either random or ordered on the surface and a film of absorbing or amplifying material whose thickness is less than the nanoparticle size.

Figure 1A:
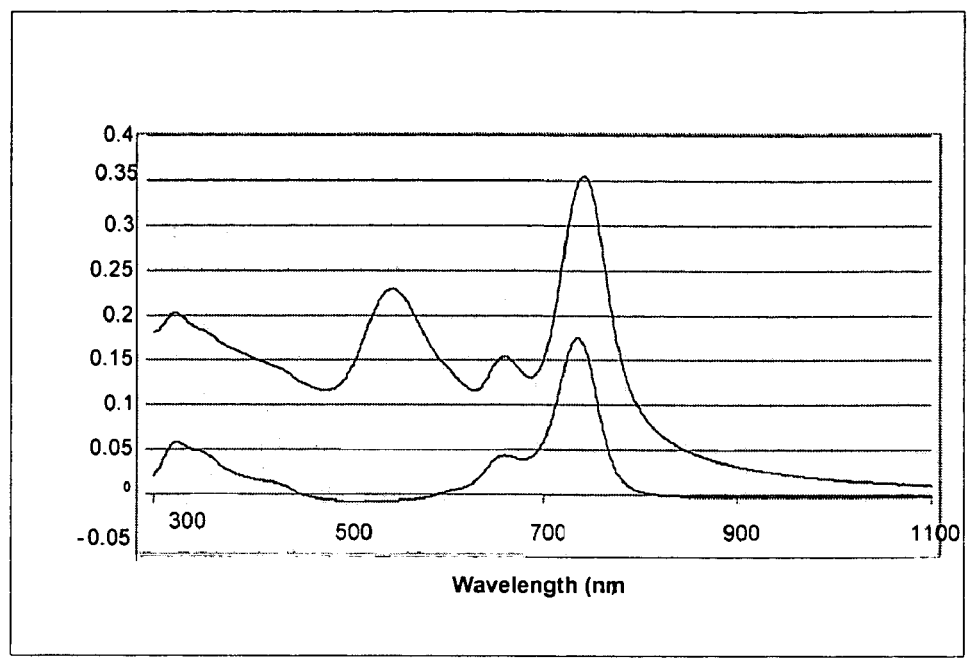
FIGS. 1a and 1b are graphical illustrations of absorbance versus wavelength for a particle surrounded by dye film.
Figure 1B:
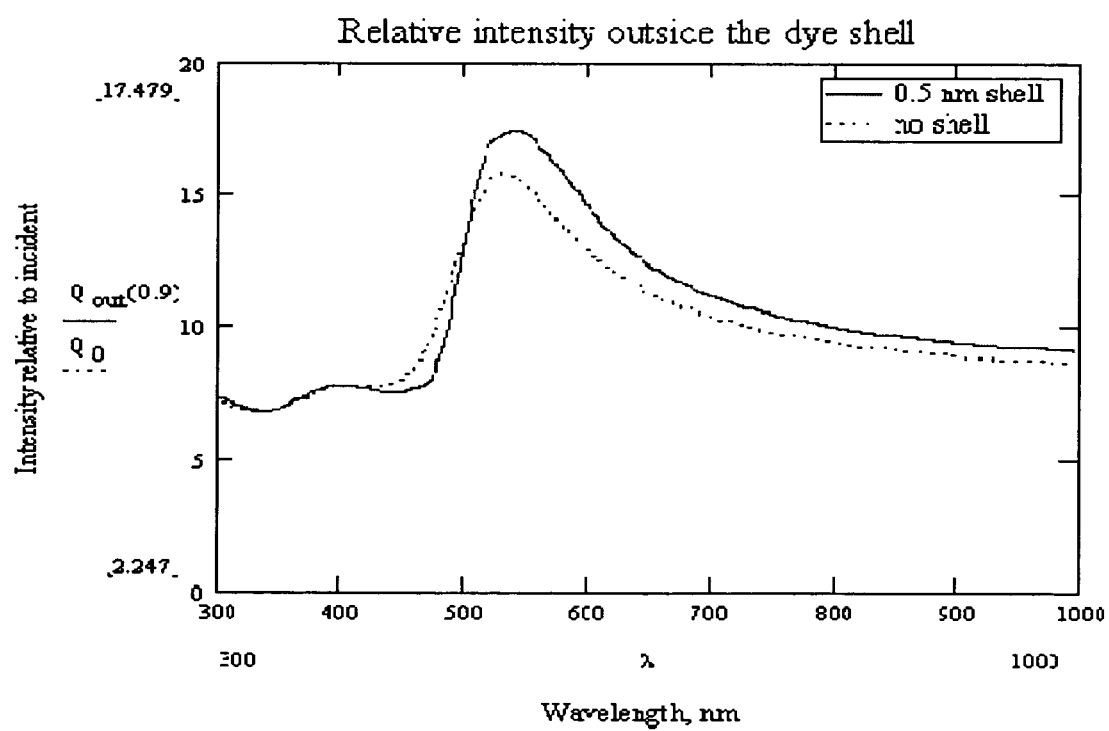
Figure 2:
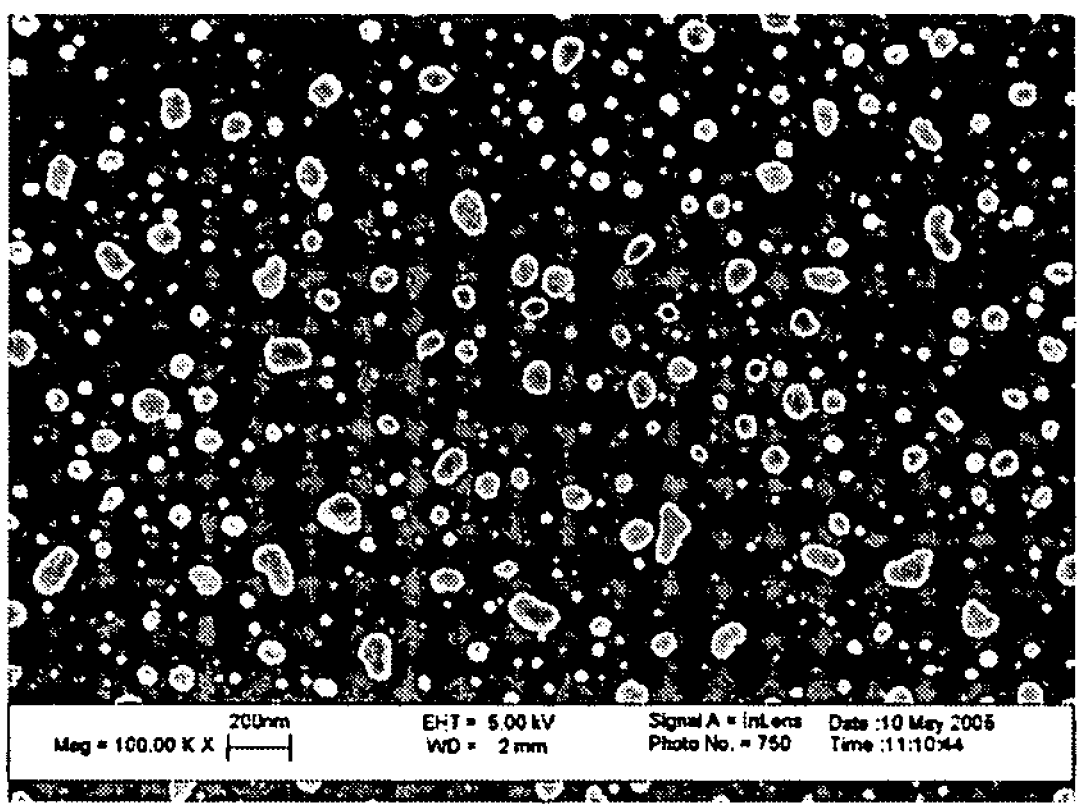
FIG. 2 is a photograph of a silicon substrate with gold particles.
Figure 3:
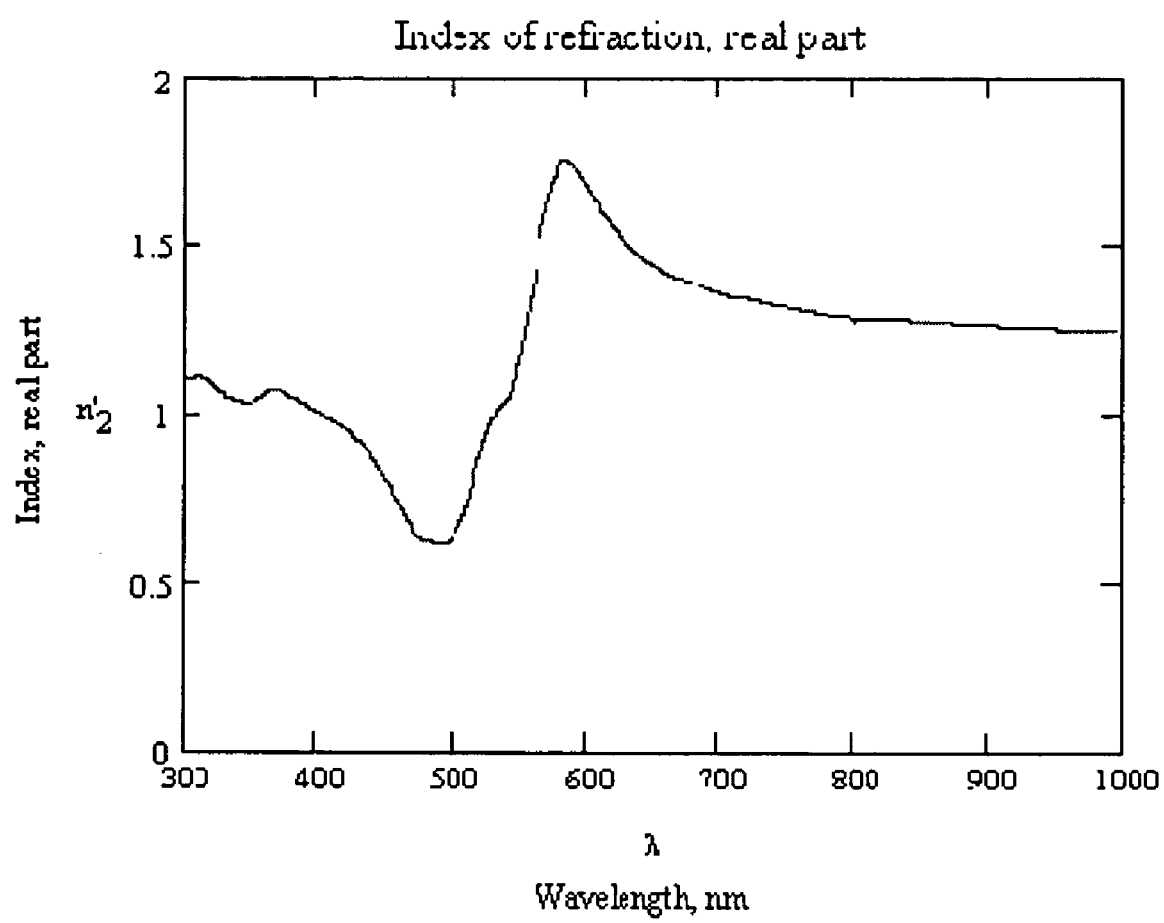
FIG. 3 shows the dielectric functions for a solid film of dye coating the particles in FIG. 1.

The exposed metallic surface can be functionalized (e.g. thiol linkers for Au particles) while the dye film allows for the amplifying effect described to occur, boosting the local fields by orders of magnitude. In addition, the film will exhibit enhanced absorption at the pump wavelength (ground state singlet absorption for a dye such as rhodamine or phthalocyanine or coumarin). It should be noted that enhanced SERS is also expected purely from an absorbing medium surrounding the particle as shown in the data of FIG. 1. This effect is again due to the presence of a strongly dispersive dielectric response of sufficient strength to provide large fields at the surface of the particle.

Similar 3-D structures can be developed to create more surface area so long as there is sufficient gain and exposed areas of metal to affect binding of the target molecules.

Several geometries are available for accessing the large local fields which arise from either an absorber film tuned to the Raman pump or signal or an amplifying film tuned to the Raman emission region. FIGS. 4a-4f show different geometries for attaching the chemical or biological moieties of interest to the active SERS substrates described.

Figure 4A:
FIGS. 4a-4f show different geometries for attaching the chemical or biological moieties of interest to the active SERS substrates described.
Figure 4B:
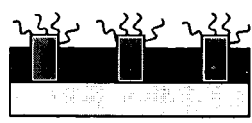
Figure 4C:
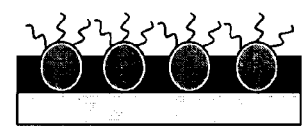

FIGS. 4a and 4c show situations where apart of the metal (Au for example) is available for the use of linkers to attach the molecules of interest (sarin, anthrax spores, DNA, proteins, etc).

Figure 4D:
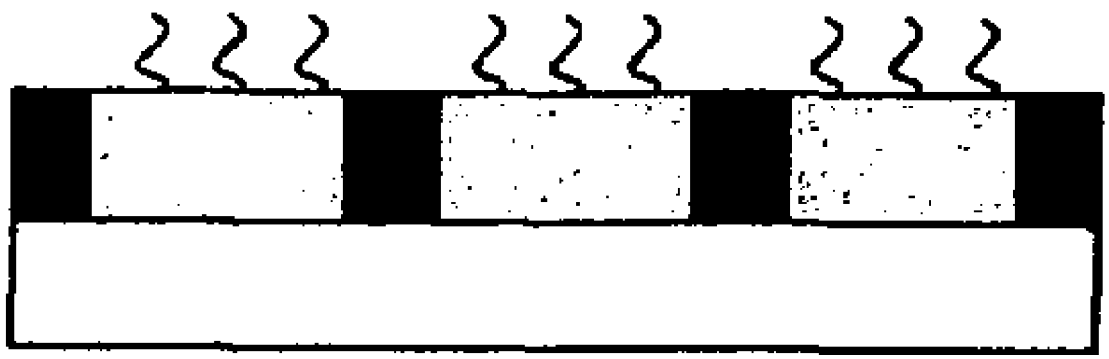

FIG. 4d shows the use of elongated nano-structures which can have different enhancement factors for different polarizations and also exhibit lower electron damping when used with amplifying media. The latter case results in a lowering of the required gain to create gigantic local fields.

Figure 4E:
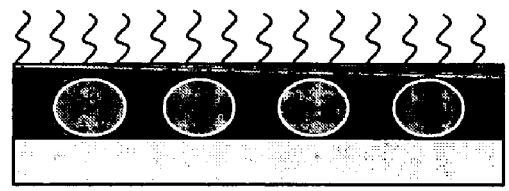
Figure 4F:
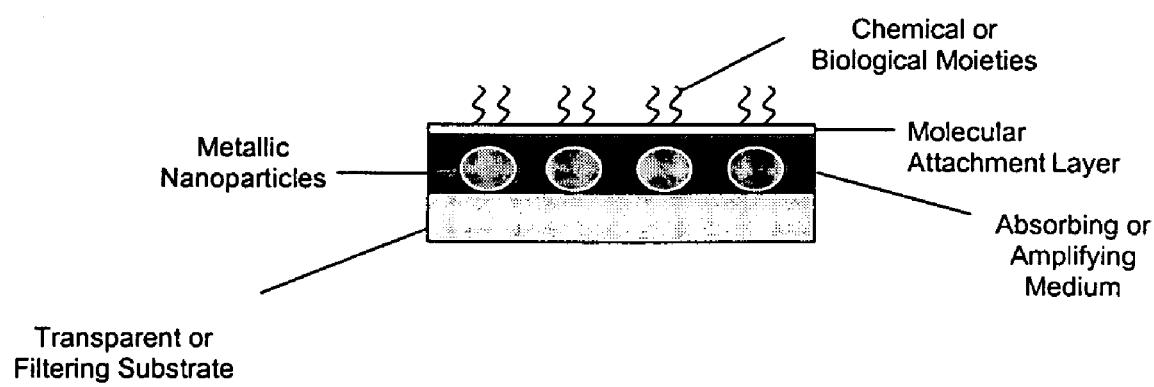

FIGS. 4e and 4f show a situation where the absorber or amplifying layer is used for attachment of the moieties of interest. Finally FIG. 4f shows the situation where a third thin film layer (<5 nm, functionalized $SiO_2$ for example) is used for binding and selectivity.

Sensor System Design

The substrates described can be used uses in compact detector systems which include spectral analysis of the SERS signals and spectral analysis software. In the case of use with only a resonant absorber film, a diode laser source can be used for excitation. When the additional gigantic enhancements achievable with a combination absorber and amplifying medium are used, there maybe a pump source for the system to function. This source can be a number of intense sources including pulses and Q switched lasers and in particular long life diode pumped solid state lasers including Raman shifters to access the required spectral bands for SERS. The substrate can be a transparent material to allow for pumping through the bottom of the structure or it can be absorbing with a long pass behavior (semiconductor doped glasses) to be used as a filter for the pump radiation when the structure is pumped from above.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A film for surface enhanced Raman scattering comprising:
    A polymeric layer; and
    A metallic nanoparticle having a cross-section and being embedded in the polymeric layer, wherein the polymeric layer has a thickness less than a largest straight line through the cross-section of said metallic nanoparticle.

2. The film of claim 1 wherein said polymeric layer is selected from a group of absorbing media and amplifying media.

3. The film of claim 1 wherein said metallic nanoparticle is gold.

4. The film of claim 1 wherein said metallic nanoparticle has a shape selected from a group of spheroids and rods.

* * * * *